United States Patent [19]

Epstein et al.

[11] Patent Number: 5,480,908
[45] Date of Patent: Jan. 2, 1996

[54] β₃-ADRENERGIC AGENTS BENZODIOXOLE DICARBOXYLATES AND THEIR USE IN PHARMACEUTICAL COMPOSITIONS

[75] Inventors: Joseph W. Epstein; Gary H. Birnberg, both of Monroe; Minu D. Dutia, West Nyack, all of N.Y.; Thomas H. Claus, Montvale, N.J.; Elwood E. Largis, Nanuet, N.Y.

[73] Assignee: American Cyanamid Company, Pearl River, N.Y.

[21] Appl. No.: 166,115

[22] Filed: Dec. 13, 1993

[51] Int. Cl.⁶ .......................... A61K 31/36; C07D 317/46
[52] U.S. Cl. .......................... 514/465; 514/466; 549/436; 549/440; 549/441; 549/446
[58] Field of Search .................. 549/436, 435, 549/434, 441, 446, 440, 60, 272; 514/465, 466, 444, 376, 360, 340, 330

[56] References Cited

U.S. PATENT DOCUMENTS

| | | | |
|---|---|---|---|
| 3,644,469 | 2/1972 | Koppa et al. | 549/435 |
| 3,872,105 | 3/1975 | Grisar et al. | 549/436 |
| 3,872,147 | 3/1975 | Koppe et al. | 549/436 |
| 4,338,333 | 7/1982 | Ainsworth et al. | 514/465 |
| 4,472,427 | 9/1984 | Baldwin et al. | 549/435 |
| 5,061,727 | 10/1991 | Bloom et al. | 514/465 |
| 5,106,867 | 4/1992 | Bloom et al. | 514/465 |
| 5,245,053 | 9/1993 | Bloom et al. | 549/435 |

FOREIGN PATENT DOCUMENTS

| | | |
|---|---|---|
| 0516350A2 | 5/1992 | European Pat. Off. . |
| 0053217 | 4/1980 | Japan . |

OTHER PUBLICATIONS

CA104(21): 186425m, Cohnen et al, (Oxadiazolyl–phenoxy) propanolamines, (1986).
CA104(19): 168191c, Koepze et al, III, 1–Phenoxy–2–hydroxy–omega–phenylalkylamunopropanes . . . , (1985).

Primary Examiner—Glennon H. Hollrah
Assistant Examiner—Deborah Lambkin
Attorney, Agent, or Firm—Hedman, Gibson & Costigan

[57] ABSTRACT

The invention is antiobesity/antidiabetes beta-3 agonists of the formula:

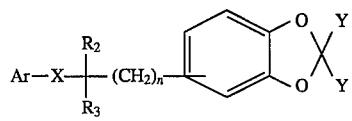

wherein Ar, X, $R_2$, $R_3$, Y and n are as defined in the specification.

6 Claims, No Drawings

β₃-ADRENERGIC AGENTS BENZODIOXOLE DICARBOXYLATES AND THEIR USE IN PHARMACEUTICAL COMPOSITIONS

BACKGROUND OF THE INVENTION

It is well known to employ medicinal agents in the treatment of persons suffering from diabetes, hyperglycemia and obesity.

Bloom et. al., U.S. Pat. No. 5,061,727, discloses compound having the general formula:

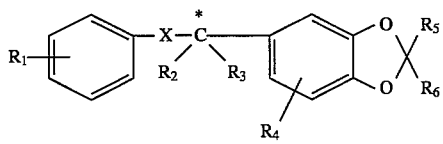

wherein $R_1$ and $R_4$ are independently hydrogen, $(C_1-C_4)$ alkyl, $(C_1-C_4)$alkoxy, hydroxy, halogen, trifluoromethyl, carboxy, hydroxyalkyl, alkoxycarbonyl, $(C_1-C_4)$thioalkyl, sulfonyl or sulfinyl; x is a divalent radical:

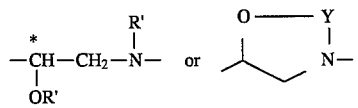

wherein R' is hydrogen, $(C_1-C_4)$ alkyl, or $(C_1-C_4)$ acyl; Y is carbonyl or thiocarbonyl; $R_2$ and $R_3$ are independently hydrogen or $(C_1-C_4)$alkyl; $R_5$ and $R_6$ are independently hydrogen, carboxy, alkoxycarbonyl, hydroxymethyl, $-CH_2OCH_2COOR_7$ or $-CH_2OCH_2CH_2OR_7$, wherein $R_7$ is hydrogen or $(C_1-C_4)$alkyl; with the proviso that $R_5$ and $R_6$ may not both be hydrogen; which are useful in the treatment of diabetes, hyperglycemia and obesity; and which show a greater degree of selectivity for the β₃-adrenergic receptor than reference agents cited within the patent.

Holloway et. al., U.S. Pat. No. 4,927,836, discloses compound having the general formula:

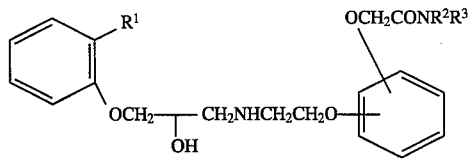

wherein $R_1$ is hydrogen or fluoro; $R_2$ is phenyl optionally bearing a substituent selected from the group consisting of halogen, $(C_1-C_4)$alkyl, $(C_1-C_4)$ alkoxy, trifluoromethyl, nitro, $(C_3-C_6)$cycloalkyl, $(C_1-C_4)$alkyl in which the carbon atom linked to the nitrogen of $NR_2R_3$ bears one or two hydrogens, or is $(C_3-C_4)$ alkenyl, either of which latter groups may optionally bear a substituent selected from the group consisting of hydroxy, $(C_1-C_4)$alkoxy, phenyl and chlorophenyl; and $R_3$ is hydrogen, methyl or ethyl; or a pharmaceutically acceptable acid addition salt thereof. They also disclose a method for producing a thermogenic effect in a warm-blooded animal requiring such treatment which comprises administering to said animal a thermogenically effective amount of a compound of the formula I, or a pharmaceutically acceptable acid addition salt thereof.

SUMMARY OF THE INVENTION

This invention is concerned with novel compounds of formula I:

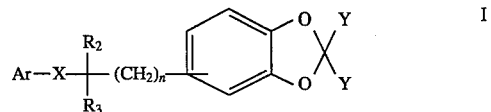

wherein: Ar is naphth-(1 or 2)-yl; substituted naphth-(1 or 2)-yl wherein the substitution is straight or branched $(C_1-C_6)$ alkyl, bromo, chloro, fluoro, iodo, $(C_1-C_6)$alkoxy, difluoromethyl or trifluoromethyl; 1,2,3,4-tetrahydro-(5 or 6)-naphthyl; substituted 1,2,3,4-tetrahydro-(5 or 6)naphthyl wherein the substitution is hydrogen, straight or branched $(C_1-C_6)$alkyl, bromo, chloro, fluoro, iodo, $(C_1-C_6)$alkoxy, difluoromethyl or trifluoromethyl; indanyl; a moiety of the formula:

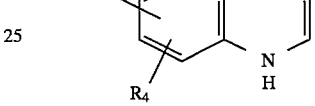

wherein $R_4$ and $R_4'$ are independently cyano, bromo, chloro, fluoro or iodo; or a moiety of the formula:

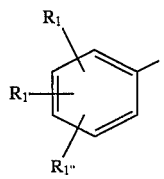

wherein $R_1$, $R_1'$, and $R_1''$ are independently hydrogen allyl; cyano; straight or branched $(C_1-C_6)$ alkyl; bromo; chloro; fluoro; iodo; $(C_1-C_6)$alkoxy; difluoromethyl; trifluoromethyl; nitro; hydroxy; $(C_1-C_6)$hydroxyalkyl; -NRSR6 wherein $R_5$ and $R_6$ are independently hydrogen, straight or branched $(C_1-C_6)$alkyl, substituted phenyl wherein the substitution is halogen, $(C_1-C_6)$ alkoxy, $(C_1-C_6)$ alkyl, trifluoromethyl or difluoromethyl; or substituted phenyl $(C_1-C_6)$alkyl wherein the substitution is halogen, $(C_1-C_6)$ alkoxy, $(C_1-C_6)$ alkyl, trifluoromethyl or difluoromethyl; sulfonyl; sulfinyl; carboxy; thienylmethyl; pyridinyl; pyridinylmethyl; furanylmethyl; tetrahydrofuranylmethyl; or $(C_1-C_6)$ alkoxycarbonyl; $R_2$ and $R_3$ are $(C_1-C_4)$alkyl; n is an integer from 0-3; Y is hydrogen; $-CO_2R_8$ wherein $R_8$ is hydrogen, straight or branched $(C_1-C_{10})$alkyl; $-CONR_9R_{10}$ wherein $R_9$ and $R_{10}$ are hydrogen, straight or branched $(C_1-C_{10})$alkyl, or methoxyethyl; with the proviso that only one Y may be hydrogen; X is a divalent radical:

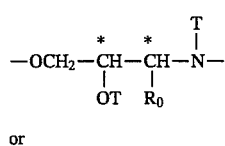

or

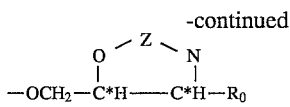

wherein $R_0$ is hydrogen or $(C_1-C_3)$alkyl; T is hydrogen, $(C_1-C_4)$alkyl, or $(C_1-C_4)$acyl; Z is carbonyl or thiocarbonyl; and the pharmaceutically acceptable salts and esters, the enantiomers, the racemic mixtures and diastereomeric mixtures thereof.

The compounds of the above formula I have centers of asymmetry at the carbon atoms marked with an asterisk (*). The compounds may, therefore, exist in at least two and often four stereoisomeric forms. The present invention encompasses all stereoisomers of the compounds whether free from other stereoisomers or admixed with other stereoisomers in any proportion and thus includes, for instance, racemic mixtures of enantiomers as well as the diastereomeric mixture of isomers. The absolute configuration of any compound may be determined by conventional X-ray crystallography.

Also according to the present invention, there is provided a method of treating diabetes and/or hyperglycemia and/or obesity and/or inflammatory bowel disease, irritable bowel syndrome, non-specific diarrhea and dumping syndrome and/or depression and/or hyperlipidemia, hypertension, hypertriglyceridemia, hypercholesterolemia, atherosclerosis and condition of low HDL in humans or other mammals and which comprises administering to a human or other mammal an anti-obesity effective amount, or an anti-hyperglycemia effective amount or an anti-inflammatory bowel disease, anti-irritable bowel syndrome, anti-non-specific diarrhea and dumping syndrome effective amount, or anti-depressant effective amount, or antihypertriglyceridemia effective amount or antihypercholesterolemia effective, or anti-atherosclerosis effective amount, or reversal-of-a-condition-of-low-HDL effective amount of a compound of the present invention.

Further, according to the present invention there are provided pharmaceutical compositions of matter comprising an effective amount of the compound of the present invention in combination with a pharmaceutically acceptable carrier; as well as a method for increasing the content of lean meat in edible mammals, which comprises administering to edible mammals an effective amount of the compound. Also, the present invention provides processes for producing the compound salts and esters of the invention.

DESCRIPTION OF THE INVENTION

The disease diabetes mellitus is characterized by metabolic defects in production and utilization of glucose which result in the failure to maintain appropriate blood sugar levels. The result of these defects is elevated blood glucose or hyperglycemia. Research on the treatment of diabetes has centered on attempts to normalize fasting and postprandial blood glucose levels. Treatments have included parenteral administration of exogenous insulin, oral administration of drugs and dietary therapies.

Two major forms of diabetes mellitus are now recognized. Type I diabetes, or insulin-dependant diabetes, is the result of an absolute deficiency of insulin, the hormone which regulates glucose utilization. Type II diabetes, or insulin-independent diabetes, often occurs in the face of normal, or even elevated levels of insulin and appears to be the result of the inability of tissues to respond appropriately to insulin. Most of the Type II diabetics are also obese.

compounds of this invention induce lipolysis in rat adipocytes in a selective manner. As effective hypoglycemic and weight loss agents, these compounds are useful for the treatment of hyperglycemia and obesity in Type II diabetes.

SELECTIVITY

β-Adrenergic receptors can be divided into $β_1$, $β_2$ and $β_3$-subtypes. Activation of $β_1$-receptors invokes increases in heart rate while activation of $β_2$-receptors stimulates glycogen breakdown in muscle and thereby prevents glycogen synthesis. Activation of $β_3$-receptors stimulates lipolysis (the breakdown of adipose tissue triglycerides to glycerol and free fatty acids), and thereby promotes the loss of fat mass. Compounds that stimulate $β_3$-receptors will have antiobesity activity. In addition, they have hypoglycemic or anti-diabetic activity, but the mechanism of this effect is unknown. A compound that selectively stimulates $β_3$-receptors, i.e. has little or no $β_1$ or $β_2$-activity, will have the desired anti-diabetic and/or anti-obesity activity, but without the undesired effects of increased heart rate ($β_1$-effect) or muscle tremor ($β_2$-effect).

Selectivity of a compound is determined using the following procedures.

Binding assays for $β_1$-effect are carried out by the use of membranes from rat heart, and $β_2$-effect by the use of membranes from rat lung by the method described in Neve, et. al., J. Pharmacol. Exp. Ther., 1985, 235, 657–664 with the following exceptions:

1. the incubation volume is 0.5 ml,
2. the incubation time is 1 hour,
3. the radioligand is $[^{125}I]$iodo-cyanopindolol,
4. (—) - isoproterenol ( 50 μM) is used to define specific binding, and
5. the filters are washed at 4° C.

The $β_3$-effect of the compounds is determined by their ability to stimulate adipocyte lipolysis. Rat epididymal fat pads are excised and placed in 0.9% saline. Four grams of tissue is transferred to a flask with 20 ml of aerated KrebsHenseleit bicarbonate (KHB) buffer containing 3% fatty acid-free bovine serum albumin to which 75 mg of crude bacterial collagenase (Worthington) has been added. The tissue is incubated for about 45 minutes at 37° C. with gentle shaking. The cells are then washed three times with two volumes of KHB buffer, filtered through two layers of gauze, and brought to a final volume of 80 ml with KHB buffer. One-ml-aliquots of the cell suspension is added to plastic test tubes containing the appropriate additions of vehicle or compound. The cells are gassed for 1 minute with 95% $O_2$–5% $CO_2$, capped, and incubated at 37° C. with continuous shaking for a total of 30 minutes. The reaction is stopped by adding 0.1 ml of 30% perchloric acid and 0.1 ml of chloroform. After centrifugation, 0.5 ml of supernatant is transferred to another test tube and neutralized with 0.04 ml of 3M $K_2CO_3$–0.5M triethanolamine. The amount of glycerol generated from the hydrolysis of endogenous triglycerides is determined in a coupled-enzyme spectrophotometric assay. One-tenth milliliter of the neutralized extract is added to a test tube that contains 0.91 ml of assay mixture comprised of the following: 0.84M glycine, 0.42M hydrazine sulfate, 4.2 mM EDTA, 0.9 mM β-NAD, 9.9 mM $MgCl_2$, 1mM ATP, 17 U of glycerophosphate dehydrogenase, and 4.3 U of glycerokinase. The test tubes are incubated for 40 minutes at 37° C. with constant shaking. The amount of NADH generated, which is proportional to the amount of glycerol, is determined by the increase in absorbance at 340 nm. This value is corrected for the amount of NADH generated in the absence of glycerol by incubating another aliquot of the neutralized extract with the same assay mixture but without glycerokinase. The molar ED50 value is the molar concentration of compound that gives 50% of the maximum rate of lipolysis of that compound.

TABLE 1

| Example No. | Lipolysis ($\beta_3$) $EC_{50}$ nM | Heart Binding ($\beta_1$) $IC_{50}$ nM | Lung Binding ($\beta_2$) $IC_{50}$ nM |
| --- | --- | --- | --- |
| 1 | 264 | 1,520 | 360 |

The lipolysis data of Table 1 suggests that weight loss and glucose reduction should be observed at a suitable level dose. The compound of Example 1, shows selectivity for the $\beta_3$-adrenergic receptor over the $\beta_1$-adrenergic receptor, however, it is not selective when compared to the $\beta_3$-receptor.

These compounds may be active in other therapeutic areas in which selective $\beta_3$-adrenergic activity is beneficial.

In addition to the abilities of the compounds described hereinabove, some of the compounds are useful as intermediates in the preparation of other compounds described in the present invention.

The compounds of the present invention may generally be prepared according to Scheme 1–5.

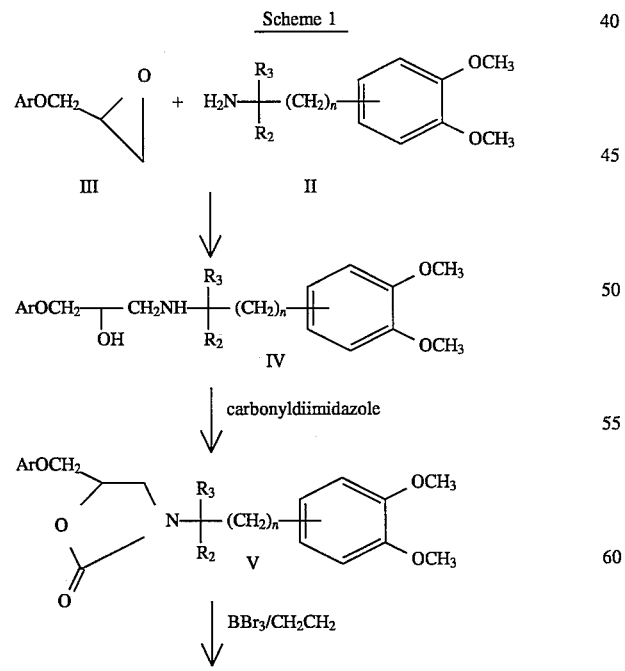

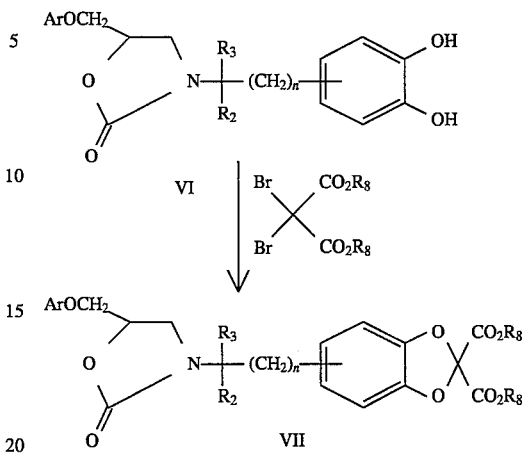

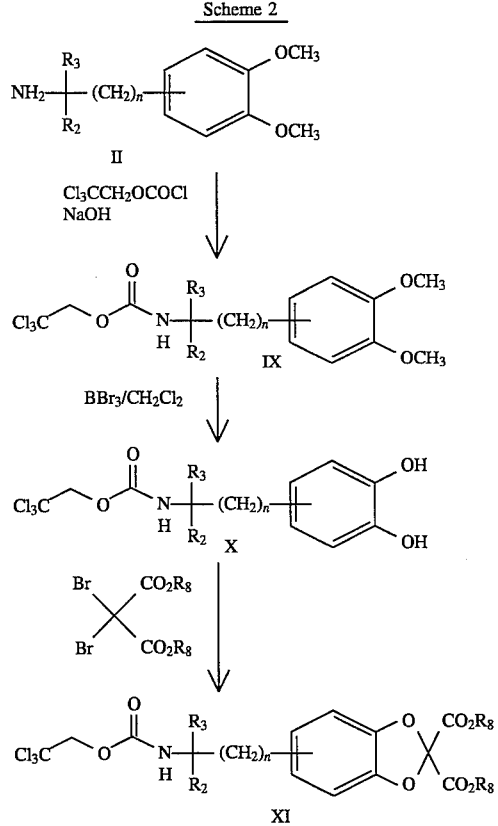

Scheme 3

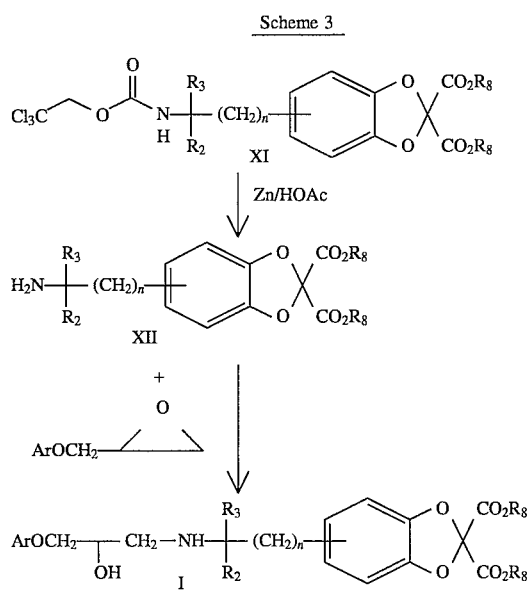

Scheme 4

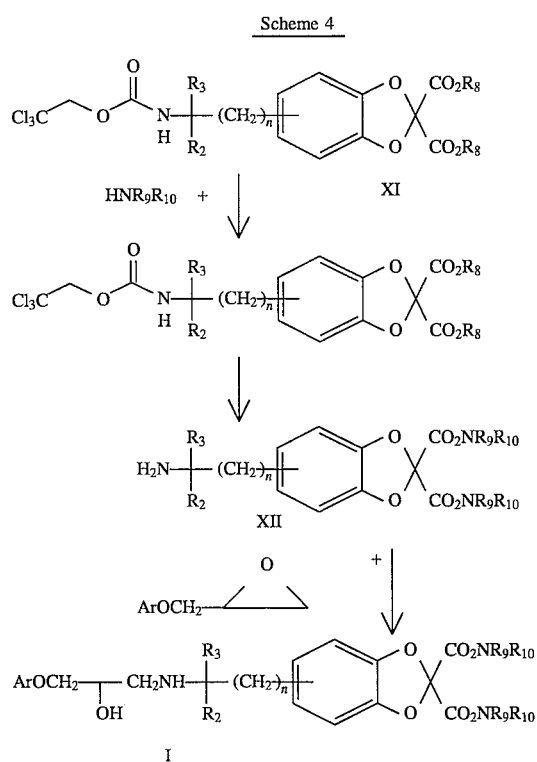

Scheme 5

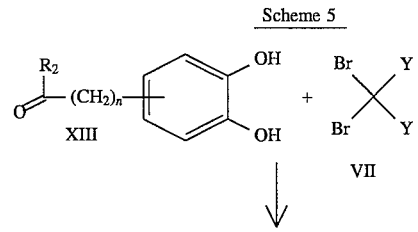

-continued
Scheme 5

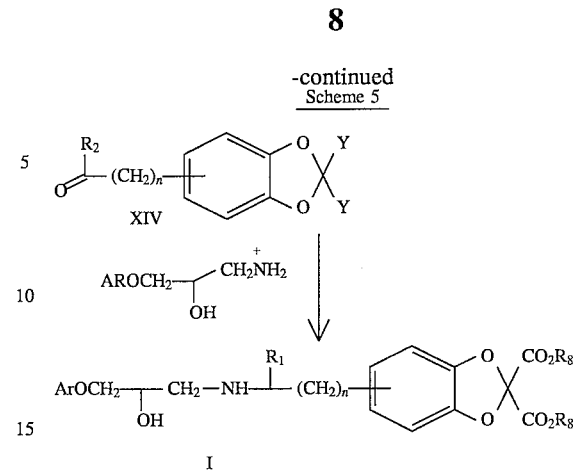

According to Scheme 1, a compound of formula

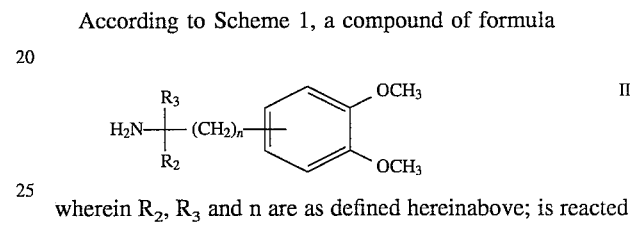

wherein $R_2$, $R_3$ and n are as defined hereinabove; is reacted with a compound of formula III:

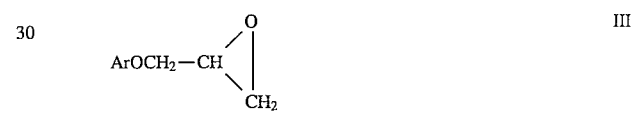

wherein Ar is as defined hereinabove; in a solvent such as ethyl alcohol, isopropyl alcohol, N,N-dimethylformamide or dimethylsulfoxide, at 80° to 120° C. for one to 36 hours, to give a compound of formula IV:

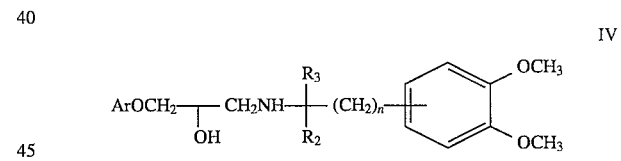

wherein Ar, $R_2$, $R_3$ and n are as defined hereinabove; and a compound of formula IV is reacted with carbonyl diimidazole in a solvent such as tetrahydrofuran at 0° to 60° C. for one to 24 hours to give a compound of formula V:

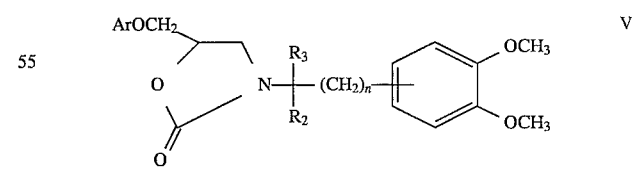

wherein Ar, $R_2$, $R_3$ and n are as defined hereinabove; and the above compound V is reacted with boron tribromide in a solvent such as methylene chloride at −10° to 5° C. for one to 5 hours to give a compound of formula VI:

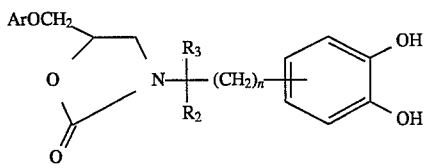                                                   VI wherein Ar, $R_2$, $R_3$ and n are as defined hereinabove; and the above compound IV is reacted with a compound of formula VII:

                                                   VII wherein Y is $-CO_2R_8$, in a solvent such as acetone, tetrahydrofuran, or dioxane, at 25° to 80° C., in the presence of a base, such as sodium carbonate, potassium carbonate, or cesium carbonate for one to 36 hours to give a compound of formula VIII:

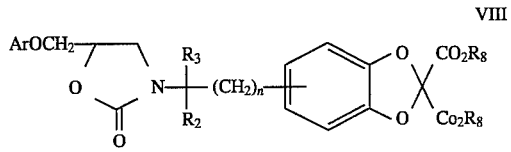                                                   VIII wherein Ar, $R_1$, $R_2$, $R_8$ and n are as defined hereinabove; the above compound is reacted with a base such as sodium hydroxide in a solvent such as an ethyl alcohol/water mixture at the reflux temperature of the solvent for from one to 24 hours to give a compound of formula I as defined hereinabove.

According to Scheme 2, a compound of formula II:

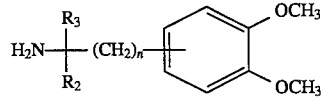                                                   II wherein $R_2$ and $R_3$ are as defined hereinabove, is reacted with a chloroformate such as $Cl_3CCH_2OCOCl$ in the presence of a base such as sodium hydroxide in a solvent such as water at 0°–40° C. for from 30 minutes to 4 hours to give a urethane of formula IX:

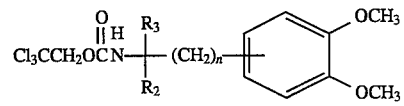                                                   IX wherein $R_2$, $R_3$ and n are as defined hereinabove, and this compound is reacted with a demethylating agent such as $BBr_3$ in a solvent such as methylene chloride at 0°–25° C. for from 30 minutes to 4 hours to give a catechl of formula X:

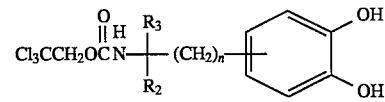                                                   X wherein $R_2$, $R_3$ and n are as defined hereinabove.

A compound of formula X is reacted with a dihalodiester of formula:

wherein Y is $-CO_2R_8$, such as diisopropyl dibromomalonate, in the presence of an acid scavenger such as potassium carbonate in a solvent such as acetone at 20°–60° C. for from one to 18 hours to give a compound of formula XI:

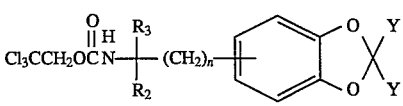                                                   XI wherein $R_2$, $R_3$, Y and n are as defined hereinabove.

According to Scheme 3, a compound of formula XI is reacted with a metal reducing agent such as zinc in an acid solution such as acetic acid at 10°–80° C. to give an amine of formula XII:

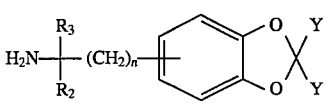                                                   XII wherein $R_2$, $R_3$, and n are as defined hereinabove and Y is $-CO_2R_8$ as defined hereinabove.

A compound of formula XII is reacted with an epoxide of formula III:

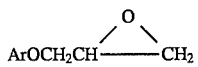

wherein Ar is as defined hereinabove, to give a compound of formula I wherein Ar, $R_2$, $R_3$, Y and n are as defined hereinabove and X is:

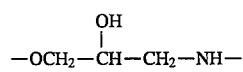

Alternatively, according to Scheme 4, a compound of formula XI, wherein $R_2$, $R_3$, and n are as defined hereinabove and Y is $-CO_2R_8$ wherein $R_8$ is as defined hereinabove, is reacted with an amine of formula:

wherein $R_9$ and $R_{10}$ are as defined hereinabove, in a solvent such as ethyl alcohol at 25°–80° C. for from one to 5 hours to give a compound of formula XI, wherein $R_2$, $R_3$ and n are as defined hereinabove, and Y is $-CONR_9R_{10}$, wherein $R_9$ and $R_{10}$ are as defined hereinabove.

A compound of formula XI, wherein Y is $CONR_9R_{10}$, is reacted with a metal reducing agent such as zinc in an acid solution such as acetic acid at 10°–80° C. to give an amine of formula XII:

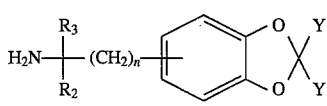

wherein $R_2$, $R_3$ and n are as defined hereinabove and Y is $CONR_9R_{10}$.

A compound of formula XII, wherein $R_2$, $R_3$ and n are as defined hereinabove and Y is $CONR_9R_{10}$, is reacted with an epoxide of formula III:

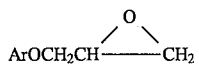

wherein Ar is as defined hereinabove, to give a compound of formula I wherein Ar, $R_2$, $R_3$, Y and n are as defined hereinabove and X is

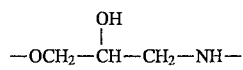

According to Scheme 5, a compound of formula XIII:

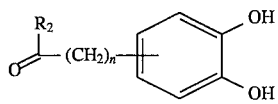

wherein $R_2$ and n are as defined hereinabove is reacted with a dihalo diester of formula:

wherein Y is $-CO_2R_8$ and $R_8$ is as defined hereinabove, to give a compound of formula XIV:

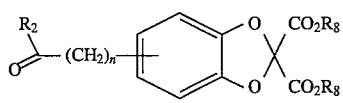

wherein $R_2$, $R_8$ and n are as defined hereinabove.

A compound of formula XIV is reacted with an aminoalcohol of formula XV:

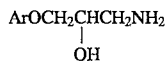

wherein Ar is as defined hereinabove, in the presence of a hydride reducing agent such as sodium borohydride, sodium cyanoborohydride, or sodium triacetoxyborohydride in a solvent such as aqueous acetic acid at 0°–25° C. for from one to 3 hours to give a compound of formula XVI:

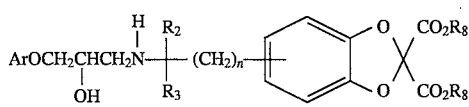

wherein Ar, $R_2$, $R_8$ and n are as defined hereinabove.

This invention will be described in greater detail in conjunction with the following examples.

Example 1

(R,R) and (S,R)-5-[2-[[2-Hydroxy-3-(1-naphthalenyloxy) propyl]amino]propyl-1,3-benzodioxole-2,2-dicarboxylic acid, disodium salt A mixture of 4.20 g of (R)-2-Amino-1-(3,4-dimethoxyphenyl)propane and 3.11 g of N-(trimethylsilyl)acetamide in 20 ml of dimethylsulfoxide is stirred at room temperature for 1 hour. A solution of 4.05 g of (1-naphthyl)glycidyl ether in 3 ml of dimethylsulfoxide is added to the above mixture and the resulting mixture is heated at 65° C. to 70° C. for 20 hours, cooled, poured into a mixture of ice and concentrated hydrochloric acid, stirred, basified with 10N sodium hydroxide and extracted with ethyl acetate. The ethyl acetate extract is washed with brine, dried, filtered and evaporated to yield 1-[(3,4-dimethoxyphenyl)-2-propyl]amino-3-(1- naphthyloxy)propan-2-ol.

A mixture of 1.4 g of the above amino alcohol, 1.39 g of carbonyldiimidazole, 3.5 ml of triethylamine and 15 ml of tetrahydrofuran is stirred overnight, then poured into water and extracted twice with ethyl acetate. The ethyl acetate extract is washed with 2N hydrochloric acid, saturated sodium chloride, dried and evaporated to an oil. The resulting oil is dissolved in methylene chloride, cooled in an ice bath and boron tribromide is added dropwise. The mixture is stirred at 0° to 5° C. for 15 minutes, then at room temperature for 20 minutes. The methylene chloride layer is separated, washed with saturated sodium chloride, dried and evaporated giving 3-[1-(3,4-dihydroxyphenyl)propyl] 5-(1-(naphthyloxymethyl)-oxazolidin-2-one.

A mixture of 0.240 g of the above oxazolidinone, 0.250 g of diethylbromomalonate, 0.500 g of anhydrous potassium carbonate and 10 ml of acetone is stirred overnight, filtered, washed with acetone and evaporated to a brown oil. The oil is purified by flash chromatography, eluting with 5% acetone/toluene. The pure fractions are combined and evaporated giving (S,R) 5-(1-naphthyloxymethyl)-2-oxo-3-oxazolidinyl)propyl) 1,3-benzodioxole-2,2-dicarboxylic acid, diethyl ester as a colorless oil.

A mixture of the above diethylester, 5N sodium hydroxide and ethyl alcohol is heated at reflux, under argon, overnight, cooled and then acidified to pH 9 using concentrated hydrochloric acid causing a copious amount of a white solid to precipitate. The mixture is filtered and the solid is washed with water. The combined titrate and water wash is loaded onto a column packed with XAD-4 non-ionic resin. The product is eluted with methanol:water (1:1). Evaporation of the combined eluates gives the desired product as a tan solid.

Example 2

(S,R,) and (R,R)-5-[2-[[3-(3-Chlorophenoxy)-2 hydroxypropyl]amino]propyl] -1,3benzodioxole-2,2-dicarboxylic acid disodium salt The title compounds are prepared by the procedure of Example 1 using 3-chlorophenyl glycidyl ether and (R)-2-amino-1-(3,4-dimethoxyphenyl)propane to give the desired products.

Example 3–20

Substantially following the method described in detail hereinabove in Example 1, using the appropriate starting material, the compound of this Invention listed below in Example 3–20 are prepared.

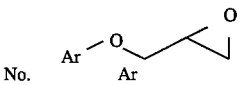

TABLE 2

| Example No. | Ar | Product of the Example |
|---|---|---|
| Example 3 | 4-methylphenyl | 5-[2-[[3-(4-methylphenoxy)-2-hydroxypropyl]-aminopropyl]-1,3-benzodioxole-2,2-dicarboxylic acid, disodium salt |
| Example 4 | 3-trifluoromethylphenyl | 5-[2-[[3-(3-trifluoromethylphenoxy)-2-hydroxypropyl]amino]propyl]-1,3-benzodioxole-2,2-dicarboxylic acid, disodium salt |
| Example 5 | 2-chloro-5-methylphenyl | 5-[2-[[3-(2-chloro-5-methylphenoxy)-2-hydroxypropyl]-amino]propyl]-1,3-benzodioxole-2,2-dicarboxylic acid, disodium salt |
| Example 6 | 4-bromophenyl | 5-[2-[[3-(4-bromophenoxy)-2-hydroxypropyl]-amino]propyl]-1,3-benzodioxole-2,2-dicarboxylic acid, disodium salt |
| Example 7 | 2,5-dichlorophenyl | 5-[2-[[3-(2,5-dichlorophenoxy)-2-hydroxypropyl]-amino]propyl]-1,3-benzodioxole-2,2-dicarboxylic acid, disodium salt |
| Example 8 | 3,4-dimethylphenyl | 5-[2-[[3-(3,4-dimethylphenol)-2-hydroxypropyl]-amino]propyl]-1,3-benzodioxole-2,2-dicarboxylic acid, disodium salt |
| Example 9 | 2-cyclopropylphenyl | 5-[2-[[3-(2-cyclopropylphenoxy)-2-hydroxypropyl]-amino]propyl]-1,3-benzodioxole-2,2-dicarboxylic acid, disodium salt |
| Example 10 | 3,5-dichlorophenyl | 5-[2-[[3-(3,5-dichlorophenoxy)-2-hydroxypropyl]-amino]propyl]-1,3-benzodioxole-2,2-dicarboxylic acid, disodium salt |
| Example 11 | 2,5-dimethylphenyl | 5-[2-[[3-(2,5-dimethylphenyl)-2-hydroxypropyl]-amino]propyl]-1,3-benzodioxole-2,2-dicarboxylic acid, disodium salt |
| Example 12 | 3-nitrophenyl | 5-[2-[[3-(3-nitrophenoxy)-2-hydroxypropyl]-amino]propyl]-1,3-benzodioxole-2,2-dicarboxylic acid, disodium salt |
| Example 13 | 3-fluorophenyl | 5-[2-[[3-(3-fluorophenoxy)-2-hydroxypropyl]-amino]propyl]-1,3-benzodioxole-2,2-dicarboxylic acid, disodium salt |
| Example 14 | phenyl | 5-[2-[[3-phenoxy-2-hydroxypropyl]-amino]propyl]-1,3-benzodioxole-2,2-dicarboxylic acid, disodium salt |
| Example 15 | 3-iodophenyl | 5-[2-[[3-(3-iodophenoxy)-2-hydroxypropyl]-amino]propyl]-1,3-benzodioxole-2,2-dicarboxylic acid, disodium salt |
| Example 16 | 4-chlorophenyl | 5-[2-[[3-(4-chlorophenoxy)-2-hydroxypropyl]-amino]propyl]-1,3-benzodioxole-2,2-dicarboxylic acid, disodium salt |
| Example 17 | 3,4-dichlorophenyl | 5-[2-[[3-(3,4-dichlorophenoxy)-2-hydroxypropyl]-amino]propyl]-1,3-benzodioxole-2,2-dicarboxylic acid, disodium salt |
| Example 18 | 1,2-dihydroinden-4-yl | 5-[2-[[3-(4-(1,2-dihydroindenyloxy))-2-hydroxypropyl]-amino]propyl]-1,3-benzodioxole-2,2-dicarboxylic acid, disodium salt |
| Example 19 | 4-(1-butyl)phenyl | 5-[2-[[3-(4-(1-butyl)phenoxy)-2-hydroxypropyl]-amino]propyl]-1,3-benzodioxole-2,2-dicarboxylic acid, disodium salt |
| Example 20 | 4-(tert-butyl)phenyl | 5-[2-[[3-(4-(tert-butyl)phenoxy)-2-hydroxypropyl]-amino]propyl]-1,3-benzodioxole-2,2-dicarboxylic acid, disodium salt |

Example 21

Diisopropyl(R).5-(2-amino)propyl,1,3-benzodioxodse-2,2- dicarboxylate

One equivalent of (R)-1-(3,4-dimethoxyphenyl) 2-aminopropane is combined with one equivalent of 2,2,2-trichloroethyl chloroformate in methylene chloride and sodium hydroxide solution. The resulting mixture is stirred at room temperature for 6 hours. The layers are separated, the organic layer is washed with dilute hydrochloric acid, dried and evaporated to give the desired urethane.

The above urethane is dissolved in methylene chloride, and then one equivalent of boron tribromide is added and this mixture is stirred at 0°–5° C. for 15 minutes, then at room temperature for 20 minutes. The reaction is quenched with water, the organic layer is dried and evaporated to give (R)-1-(3,4-dihydroxy- phenyl)-2-(2,2,2-trichloroethoxycarbonyl)amino propane.

The above catechol is combined with one equivalent of diisopropyl dibromomalonate in acetone and powdered, anhydrous potassium carbonate. The reaction mixture is stirred at room temperature for 18 hours. Filtration and evaporation of the solution gives diisopropyl 5-((2,2,2-trichloroethoxycarbonyl)amino)- propyl-1,3-benzodioxole-2,2-dicarboxylate.

This diester is stirred in a mixture of powdered zinc in acetic acid/tetrahydrofuran/water for 6 hours at room temperature. The mixture is filtered, and the filtrate is neutralized with sodium bicarbonate. Isolation of the product gives the desired product. $^1$H NMR(CDCl$_3$):δ 6.86(d,1H, J=8.0Hz); 6.79(d,1H, J=1.3Hz); 6.71(dd, 1H, J=1.3 and 8.0Hz); 5.19(septet,2H, J=6.3Hz ); 3.07–3.13 (m, 1H); 2.64 (dd, 1H, J=13.4 and 5.2Hz); 2.44(dd,1H, J=13.4 and 8.1Hz); 1.32(d,12H, J=6.3Hz); 1.10(d,3H, J=6.3Hz).

Example 22

(R)-5-(2-amno)propyl-1,3benzodioxole-2,2(N-N'-dibutyl) dicarboxamide

One equivalent of diisopropyl 5-(2,2,2-trichloro-ethoxycarbonylamino) propyl-1,3-benzodioxole2,2-dicarboxylate of Example 21 in excess n-butylamine is heated at reflux for 8 hours. The excess n-butylamine is removed in vacuo giving 5-(2,2,2-trichloro-ethoxycarbonyl)amino)-propyl-1,3-benzodioxole-2,2-(N,N'-dibutyl)dicarboxamide This protected amino-bisamide, 2.40 g, is dissolved in 40 ml of tetrahydrofuran and to this is added 6 ml of acetic acid and 6 ml of water, followed by 4.4 g of activated zinc dust. The mixture is stirred at ambient temperature for 1 hour, then an additional 3.5 g of zinc dust is added and the stirring is continued for an additional 2 hours. The solvents are removed in vacuo and the residue is treated with 250 ml of water, 100 ml of saturated sodium bicarbonate solution and 250 ml of chloroform. The mixture is filtered, the organic layer is separated, washed with brine, dried and evaporated to give the desired product as a yellow oil. $^1$H NMR(CDCl$_3$):δ6.86(d, 1H, J=8.0Hz); 6.79(d, 1H, J=1.2Hz); 6.74(dd,1H, J=1.4 and 8.0Hz); 3.31(1,4H, J=7.0Hz); 3.19–3.05 (m, 1H); 2.64 (dd, 1H, CH$_2$Ar, J=13.4 and 5.4Hz ); 2.47 (dd, 1H, CH$_2$Ar, J=13.4 and 8.0Hz ); 1.88 (vbr, 2H, NH$_2$ ); 1.59–1.47 (m, 4H); 1.40–1.26 (m, 4H); 1.11 (d, 3H, CH$_3$, J=6.3Hz); 0.09(t,6H,CH $_3$, j=7.4Hz).;

Examole 23

(S,R) and (R, R) -5- [2- [[3- (2-Allylphenoxy) -2hydroxypropyl ] amino ] propyl]-1,3 -benzodioxole-2,2 - [ (N, N' -dibutyl) dicarboxamide ]

The epoxide, 0.48 g ,is dissolved in 4 ml of acetonitrile, and to this is added 0.56 g magnesium perchlorate, stirred until dissolved, then the amino-bis amide ,0.95 g, dissolved in 10 ml acetonitrile is added. The reaction mixture is stirred overnight, then quenched into water. The mixture is extracted with diethyl ether then methylene chloride, and the combined organic layers are washed with water, saturated sodium chloride, dried over sodium sulfate, filtered and evaporated. The crude product is dissolved in chloroform and chromatographed on silica gel eluting with 10% methanol in chloroform. Cuts containing product are combined and evaporated to give 0.50g of the desired product as a solid. $^1$H NMR (CDCl$_3$)δ7.23–1.12(m,2H); 7.10–6.70(m, 7H,ArH); 6.05–5.89 (m, 1H); 5.09–4.97 (m, 2H); 3.92–4.08 (m, 3H); 3.43– 3.34(m,2H,ArOCH$_2$); 3.31(q,4H, J=7.0Hz); 2.98–2.67(m,4H); 2.59–2.50 (m, 1H); 1.59–1.46 (m, 4H); 1.40–1.25 (m, 4H); 1.06(d,3H,CH$_3$); 0.89(t,6H, J=7.3Hz).

Example 24

(S,R) -5- [2- [ [3 - (2-Allylphenoxy)) -2-hydroxvpropyl] amino ] propyl ] -1,3 -benzodioxole-2,2 -dicarboxylic acid, disodium salt (S,R) - 5 - [ 2 - [ [ 3 - ( 2 -Allylphenoxy ) -2 -hydroxypropyl ] -amino ] propyl ] - 1,3 -benzodioxole -2,2 - [ (N, N'- dibutyl)-dicarboxamide], 0.35 g, is mixed with 10 ml of 2.5N sodium hydroxide and heated to gentle reflux for 18 hrs. The reaction mixture is diluted with 100 ml of water and treated with 50 g of XAD-4 Resin (previously washed with water, methanol/water, then water). This slurry is then filtered, washed with water (-500mL), and then washed with methanol. The methanol eluate is evaporated to give 0.071 g. of the title compound as a light brown solid. $^1$H NMR(D$_2$O):δ7.33–7.23(m,2H); 7.08–66.60(m,5H,ArH); 6.43–6.24 (m, ½H,SR and RR: CH$_2$CH=CH$_2$); 6.11–5.91 (m, ½ H, CH$_2$CH=CH$_2$); 5.09– 4.85 (m,2H,CH$_2$CH=CH$_2$); 4.16–3.76(m,4H); 3.40–3.31(m, 1H); 3.05–2.56(m,5H); 1.09(d,3H,CH$_3$, J=6.2Hz).

Examples 25–36

Substantially following the methods described in detail hereinabove in Examples 21–24, using the appropriate arylglycidyl ether, the compounds of this invention listed in Examples 25–36 are prepared.

TABLE 3

Ar—O—CH$_2$—CH(O)—CH$_2$

| Example No. | Ar | Product of the Example |
|---|---|---|
| Example 25 | 4-methoxyphenyl | 5-[2-[[3-(4-methylphenoxy)-2-hydroxypropyl]-amino]propyl]-1,3-benzodioxole-2,2-dicarboxylic acid, disodium salt |
| Example 26 | 3-methoxyphenyl | 5-[2-[[3-(3-methoxyphenoxy)-2-hydroxypropyl]-amino]-propyl]-1,3-benzodioxole-2,2-dicarboxylic acid, disodium salt |
| Example 27 | 2,5-dimethoxyphenyl | 5-[2-[[3-(2,5-dimethoxyphenoxy)-2-hydroxy-propyl]amino]propyl]-1,3-benzodioxole-2,2-dicarboxylic acid, disodium salt |
| Example 28 | 3-cyanophenyl | 5-[2-[[3-(3-cyanophenoxy)-2-hydroxypropyl]amino]-propyl]-1,3-benzodioxole-2,2-dicarboxylic acid, disodium salt |
| Example 29 | 5,6,7,8-tetrahydro- | 5-[2-[[3-(1-(5,6,7,8-tetrahydronaphthyloxy))-2- |

TABLE 3-continued

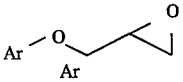

| Example No. | Ar | Product of the Example |
|---|---|---|
| | naphth-1-yl | hydroxypropyl]amino]propyl]-1,3-benzodioxole-2,2-dicarboxylic acid, disodium salt |
| Example 30 | 2-cyclopentylphenyl | 5-[2-[[3-(2-cyclopentylphenoxy)-2-hydroxypropyl]amino]propyl]-1,3-benzodioxole-2,2-dicarboxylic acid, disodium salt |
| Example 31 | 2-(2-thienyl-methyl)phenyl | 5-[2-[[3-(2-(2-thienylmethyl)phenoxy)-2-hydroxypropyl]amino]-propyl]-1,3-benzodioxole-2,2-dicarboxylic acid, disodium salt |
| Example 32 | 2-(2-pyridinyl-methyl)phenyl | 5-[2-[[3-(2-(2-pyridinylmethyl)phenoxy)-2-hydroxypropyl]amino]propyl]-1,3-benzodioxole-2,2-dicarboxylic acid, disodium salt |
| Example 33 | 2-(2-furanylmethyl)-phenyl | 5-[2-[[3-(2-(2-furanylmethyl)phenoxy)-2-hydroxypropyl]amino]propyl]-1,3-benzodioxole-2,2-dicarboxylic acid, disodium salt |
| Example 34 | 2-(2-tetrahydro-furanylmethyl)phenyl | 5-[2-[[3-(2-(2-tetrahydrofuranylmethyl)phenoxy)-2-hydroxypropyl]amino]propyl]-1,3-benzodioxole-2,2-dicarboxylic acid, disodium salt |
| Example 35 | 2-(2-pyridinyl)phenyl | 5-[2-[[3-(2-(2-pyridinyl)phenoxy)-2-hydroxypropyl]amino]propyl]-1,3-benzodioxole-2,2-dicarboxylic acid, disodium salt |
| Example 36 | 4-methoxymethylphenyl | 5-[2-[[3-(4-methoxymethylphenoxy)-2-hydroxypropyl]amino]propyl]-1,3-benzodioxole-2,2-dicarboxylic acid, disodium salt |

Example 37

5-(2-(1-Naphtholoxy)-2-hydroxyethyl)aminomethyl-1,3=benzodioxole-2,2-dicarboxylic acid, disodium salt One equivalent of 3,4-dihydroxybenzaldehyde, 1.1 equivalents of diethyl dibromomalonate and powdered potassium carbonate is stirred in acetonitrile at room temperature for 18 hours. The reaction mixture is filtered, evaporated in vacuo and distilled to give diethyl 5-formyl-1,3-benzodioxole-2,2-dicarboxylate. $^1$H NMR(CDCl$_3$):δ9.9(s,1H,CHO); 7.5(m,2H, aromatic H) ; 7.1(d, 1H,aromatic H) ; 4.45(q,4H,CH$_2$); 1.8(t,6H,CH$_3$).

One equivalent of the above aldehyde, one equivalent of 2-amino-1-(1-naphthyloxy)ethanol, one equivalent of acetic acid and 1.5 equivalents of sodium triacetoxyborohydride in 1,2-dichloroethane is stirred at room temperature for 1 hour. The solvent is evaporated in vacuo. The residue is dissolved in 2.5N sodium hydroxide in ethyl alcohol, heated at reflux temperature for one hour, and evaporated in vacuo. The residue is purified on an ion exchange column to give the desired product.

Example 38

5-[2-[[3-Phenoxy-2-hydroxypropyl]aminooropyl]-1,3- benzodioxole-2,2-dicarboxylic acid, diisooropyl ester A solution of one equivalent of diisopropyl 5(2-amino) propyl-1,3-benzodioxole-2,2-dicarboxylate and one equivalent of phenyl glycidyl ether in ethanol is heated at reflux temperature for 8 hours. The solution is evaporated in vacuo to give the desired compound.

We claim:
1. A compound of the formula:

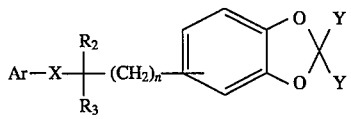

wherein: Ar is naphth-(1 or 2)-yl; substituted naphth-(1 or 2)-yl wherein the substitution is straight or branched (C$_1$–C$_6$) alkyl, bromo, chloro, fluoro, iodo (C$_1$–C$_6$)alkoxy, difluoromethyl or trifluoromethyl; 1,2,3,4-tetrahydro-(5 or 6)-naphthyl; substituted 1,2,3,4-tetrahydro-(5 or 6)naphthyl where the substitution is hydrogen, straight or branched (C$_1$–C$_6$) alkyl, bromo, chloro, fluoro, iodo, (C$_1$–C$_6$) alkoxy, difluoromethyl or trifluoromethyl; R$_2$ and R$_3$ are (C$_1$–C$_4$)alkyl; n is an integer from 0–3; Y is hydrogen; -CO$_2$R$_8$ wherein R$_8$ is hydrogen, straight or branched (C$_1$C$_{10}$)alkyl; or CONR$_9$R$_{10}$ wherein R$_9$ and R$_{10}$ are hydrogen, straight or branched (C$_1$–C$_{10}$) alkyl, or methoxymethyl,; with the proviso that only one Y may be hydrogen; X is a divalent radical;

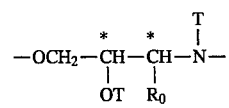

wherein R$_O$ is hydrogen or (C$_1$–C$_6$) alkyl; T is hydrogen, (C$_1$–C$_4$) alkyl, or (C$_1$–C$_4$)acyl; and the pharmaceutically acceptable salts and esters, the enantiomers, the racemic mixtures and diasterromeric mixtures thereof.

2. A compound according to claim 1, (R,R) and (S,R)-5-[2-[[2-hydroxy-3-(1- naphthalenyloxy)propyl]amino]propyl-1,3-benzodioxole-2,2- dicarboxylic acid, disodium salt.

3. A method for treating hyperglycemia in mammals which comprises administering to a hyperglycemic patient an antihyperglycemic effective amount of a compound of claim 1.

4. A method for treating diabetes in mammals which comprises administering to a diabetic patient an antidiabetic effective amount of a compound of claim 1.

5. A method of treating obesity in mammals which comprises administering to an obese patient an antiobesity effective amount of a compound of claim 1.

6. A method of increasing lean meat in edible animals which comprises administering to an animal an antilipogenic effective amount of a compound of claim 1.

* * * * *